(12) United States Patent
Hermann et al.

(10) Patent No.: US 6,562,601 B2
(45) Date of Patent: May 13, 2003

(54) FERMENTATION PROCESS FOR THE PREPARATION OF L-THREONINE

(75) Inventors: Thomas Hermann, Bielefeld (DE); Mechthild Rieping, Bielefeld (DE)

(73) Assignee: Degussa AG, Dusseldorf (DE)

( * ) Notice: Subject to any disclaimer, the term of this patent is extended or adjusted under 35 U.S.C. 154(b) by 23 days.

(21) Appl. No.: 09/935,758

(22) Filed: Aug. 24, 2001

(65) Prior Publication Data

US 2002/0055151 A1 May 9, 2002

Related U.S. Application Data
(60) Provisional application No. 60/236,039, filed on Sep. 28, 2000.

(30) Foreign Application Priority Data

Aug. 31, 2000 (DE) .......................................... 100 42 745
Jan. 27, 2001 (DE) .......................................... 101 03 778

(51) Int. Cl.$^7$ ............................ C12P 13/08; C12N 1/20
(52) U.S. Cl. ................................. 435/115; 435/252.33
(58) Field of Search .............................. 435/252.33, 115

(56) References Cited

U.S. PATENT DOCUMENTS

| | | | | |
|---|---|---|---|---|
| 4,996,147 A | * | 2/1991 | Furukawa et al. | ........... 435/115 |
| 5,175,107 A | * | 12/1992 | Debabov et al. | ....... 435/252.33 |
| 5,538,873 A | * | 7/1996 | Debabov et al. | ............ 435/115 |
| 5,631,157 A | * | 5/1997 | Debabov et al. | ....... 435/252.33 |
| 5,939,307 A | * | 8/1999 | Wang et al. | ........... 435/252.33 |

FOREIGN PATENT DOCUMENTS

| | | |
|---|---|---|
| EP | 0 593 792 | 4/1994 |
| EP | 0 593 792 B1 * | 5/1997 |
| EP | 1 085 091 | 3/2001 |
| GB | 1 009 370 | 11/1965 |
| WO | WO 00/09660 * | 2/2000 |
| WO | WO 02 26993 | 4/2002 |

OTHER PUBLICATIONS

Chung C. T. et al. One step preparation of comptetent *Escherichia coli*: Transformation and storage of bacterial cells in the same solution, Proc. Natl. Acad. Sci. USA, 1989, 86: 2172–2175.*

Okamoto K. et al. Hyperproduction of L–threonine by an *Escherichia coli* mutant with impaired L–threonine uptake, Biosc. Biotech. Biochem. 1997, 61, 1877–1882.*

Gerdes K. The parB(hok/sok) locus of plasmid R1: a general purpose plasmid stabilization system, Bio/Technology, 1988, 5, 1402–1405.*

English language abstract of reference PR above.

* cited by examiner

*Primary Examiner*—Tekchand Saidha
*Assistant Examiner*—Malgorzata A. Walicka
(74) *Attorney, Agent, or Firm*—Pillsbury Winthrop LLP

(57) ABSTRACT

The invention relates to a process for the fermentative preparation of L-threonine in which an L-threonine-producing microorganism of the Enterobacteriaceae family is cultured by the feed process, and a portion of the fermentation broth is then separated off in order to be utilized for inoculation of further media.

18 Claims, No Drawings

FERMENTATION PROCESS FOR THE PREPARATION OF L-THREONINE

CROSS REFERENCE TO RELATED APPLICATIONS

The present application claims the benefit under 35 U.S.C. §119(e) of U.S. provisional application No. 60/236,039, filed on Sep. 28, 2000. In addition, the application claims priority to German application DE 100 42 745.6, filed on Aug. 31, 2000 and also to German application DE 101 03 778.3, filed on Jan. 27, 2001.

Field of the Invention

The invention provides a new process for the fermentative preparation of L-threonine with Enterobacteriaceae.

PRIOR ART

L-Threonine is used in animal nutrition, in human medicine and in the pharmaceuticals industry.

It is known that L-threonine can be prepared by fermentation of strains of the Enterobacteriaceae family, in particular *Escherichia coli*. Because of the great importance of this amino acid, work is constantly being undertaken to improve the preparation processes. Improvements to the process can relate to fermentation measures, such as e.g. stirring and supply of oxygen, or the composition of the nutrient media, such as e.g. the sugar concentration during the fermentation, or the working up to the product form, by e.g. ion exchange chromatography, or the intrinsic output properties, i.e. those of genetic origin, of the microorganism itself.

It is known from the prior art, such as is described, for example, in U.S. Pat. No. 5,538,873 and in EP-B-0593792 or by Okamoto et al. (Bioscience, Biotechnology, and Biochemistry 61 (11), 1877—1882, 1997), that threonine is prepared by fermentation in the batch process (batch) or feed process (fed batch).

OBJECT OF THE INVENTION

The inventors had the object of providing new measures for improved fermentative preparation of L-threonine.

SUMMARY OF THE INVENTION

The invention provides a fermentation process, which is characterized in that
  a) an L-threonine-producing microorganism of the Enterobacteriaceae family is cultured by the feed process (fed batch) in a known manner, subsequently
  b) a portion of the fermentation broth is separated off, 1 to 90 vol. %, in particular 1 to 50 vol. %, preferably 1 to 25 vol. % and particularly preferably 5 to 50 vol. % of the total volume of the fermentation broth remaining in the fermentation tank, subsequently
  c) the remaining fermentation broth is topped up with growth medium and, preferably after a growth phase, a further fermentation is carried out by the feed process (fed batch) mentioned,
  d) steps b) and c) are optionally carried out several times, and
  e) the L-threonine is isolated from the fermentation broths collected.

DETAILED DESCRIPTION OF THE INVENTION

The microorganisms with which the process according to the invention can be carried out can prepare L-threonine from glucose, sucrose, lactose, fructose, maltose, molasses, starch, or from glycerol and ethanol, the preparation from glucose, sucrose or molasses being preferred. They are representatives of Enterobacteriaceae, in particular of the genera Escherichia, Serratia and Providencia. Of the genus Escherichia the species *Escherichia coli* and of the genus Serratia the species Serratia marcescens are to be mentioned in particular.

Suitable L-threonine-producing strains of the genus Escherichia, in particular of the species *Escherichia coli*, are, for example
  *Escherichia coli* TF427
  *Escherichia coli* H-4225
  *Escherichia coli* H-4226
  *Escherichia coli* H-4257
  *Escherichia coli* H-4258
  *Escherichia coli* H-4435
  *Escherichia coli* H-4436
  *Escherichia coli* H-4578
  *Escherichia coli* H-7256
  *Escherichia coli* H-7263
  *Escherichia coli* H-7293
  *Escherichia coli* H-7294
  *Escherichia coli* H-7700
  *Escherichia coli* H-7729
  *Escherichia coli* H-8309
  *Escherichia coli* H-8311
  *Escherichia coli* H-9244
  *Escherichia coli* KY10935
  *Escherichia coli* EL1003
  *Escherichia coli* VNIIgenetika MG-442
  *Escherichia coli* VNIIgenetika VL334/pYN7
  *Escherichia coli* VNIIgenetika M1
  *Escherichia coli* VNIIgenetika 472T23
  *Escherichia coli* VNIIgenetika TDH-
  *Escherichia coli* BKIIM B-3996
  *Escherichia coli* BKIIM B-5318
  *Escherichia coli* B-3996-C43
  *Escherichia coli* B-3996-C80
  *Escherichia coli* B-3996/pTWV-pps
  *Escherichia coli* B-3996(pMW::THY)
  *Escherichia coli* B-3996/pBP5
  *Escherichia coli* Ferm BP-3756
  *Escherichia coli* Ferm BP-4072
  *Escherichia coli* Ferm BP-1411
  *Escherichia coli* kat 13
  *Escherichia coli* KCCM-10132
  *Escherichia coli* KCCM-10133.

Suitable L-threonine-producing strains of the genus Serratia, in particular of the species *Serratia marcescens*, are, for example
  *Serratia marcescens* HNr21
  *Serratia marcescens* TLr156
  *Serratia marcescens* T2000

Strains from the Enterobacteriaceae family which produce L-threonine preferably have, inter alia, one or more genetic or phenotypic features chosen from the group consisting of: resistance to α-amino-β-hydroxyvaleric acid, resistance to thialysine, resistance to ethionine, resistance to α-methylserine, resistance to diaminosuccinic acid, resistance to a-aminobutyric acid, resistance to borrelidin, resistance to rifampicin, resistance to valine analogues, such as, for example, valine hydroxamate, resistance to purine analogues, such as, for example, 6-dimethylaminopurine, a need for L-methionine, optionally a partial and compensatable need for L-isoleucine, a need for meso-diaminopimelic acid, auxotrophy in respect of threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally an ability for sucrose utilization, enhancement of the threonine operon, enhancement of homoserine dehydrogenase I-aspartate kinase I, preferably of the feed back resistant form, enhancement of homoserine kinase, enhancement of threonine synthase, enhancement of aspartate kinase, optionally of the feed back resistant form, enhancement of aspartate semialdehyde dehydrogenase, enhancement of phosphoenol pyruvate carboxylase, optionally of the feed back resistant form, enhancement of phosphoenol pyruvate synthase, enhancement of transhydrogenase, enhancement of the RhtB gene product, enhancement of the RhtC gene product, enhancement of the YfiK gene product, enhancement of a pyruvate carboxylase, and attenuation of acetic acid formation.

Thus, for example, the strain 472T23 (U.S Pat. No. 5,631,157) has, inter alia, an enhanced, "feed back" resistant aspartate kinase I-homoserine dehydrogenase I, an attenuated threonine deaminase, a resistance to at least 5 g/l L-threonine and the ability to utilize sucrose as a source of carbon.

Thus, for example, the strain B-3996 (U.S. Pat. No. 5,175,107) has, inter alia, an enhanced, "feed back" resistant aspartate kinase I-homoserine dehydrogenase I, an attenuated threonine deaminase, an attenuated threonine dehydrogenase, a resistance to at least 5 g/l L-threonine and the ability to utilize sucrose as a source of carbon.

Thus, for example, the strain kat-13 (U.S. Pat. No. 5,939, 307) has, inter alia, an enhanced, "feed back" resistant aspartate kinase I-homoserine dehydrogenase I, an attenuated threonine dehydrogenase, resistance to borrelidin and the ability to utilize sucrose as a source of carbon.

Thus, for example, the strain KCCM-10132 (WO 00/09660) has a resistance to α-methylserine, a resistance to diaminosuccinic acid, sensitivity to fluoropyruvate, a resistance to L-glutamic acid and a resistance to at least 7% L-threonine. The strain is also in need of the amino acids L-methionine and L-isoleucine.

The term "enhancement" in this connection describes the increase in the intracellular activity of one or more enzymes in a microorganism which are coded by the corresponding DNA, for example by increasing the number of copies of the gene or allele or of the genes or alleles, using a potent promoter or using a gene or allele which codes for a corresponding enzyme having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

According to the invention, the system output of a fermentation unit producing L-threonine is increased by a procedure in which after a first fermentation step a portion of the fermentation broth obtained in this way remains in the production fermenter and serves as the inoculum for one or more further fermentation steps (batches).

According to the invention, 1 to 90 vol. %, preferably 1 to 50 vol. %, preferentially 1 to 25 vol. %, 1 to 20 vol. %, 1 to 15 vol. % or 1 to 10 vol. %, and particularly preferably 5 to 20 vol. %, 5 to 15 vol. % or 1 to 10 vol. % of the total volume of the fermentation broth remains in the fermentation tank.

The broth remaining in the fermentation tank is preferably topped up with a growth medium. After optionally >0 to not more than 10 hours, preferably after 1 to 10 hours, preferentially 2 to 10 hours and particularly preferably 3 to 7 hours a production medium is fed in. Alternatively, the components of this medium can also be fed in separately. After 20 to 72 hours, preferably 20 to 48 hours, the batch is ended and a portion of the fermentation broth, as described above, is separated off. A new fermentation stage is then optionally started with the remainder. The process can be repeated at least once, preferably approx. 2 to 6 times, depending on the stability of the strain used. Repetitions of approx. 2 to 8 times or 2 to 10 times or 2 to 4 times are also possible.

Appropriately stable strains which do not lose their production properties in the course of the process are particularly suitable for the process described.

The growth medium typically comprises sugars, such as e.g. glucose, starch hydrolysate, sucrose or molasses, as the source of carbon. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus.

The culture medium must furthermore comprise salts of metals, such as e.g. magnesium sulfate, manganese sulfate or iron sulfate, which are necessary for growth. Finally, essential growth substances, such as amino acids (e.g. homoserine) and vitamins (e.g. thiamine), are employed in addition to the above-mentioned substances. Antifoams, such as e.g. fatty acid polyglycol esters, can be employed to control the development of foam.

In general, the production medium comprises only one sugar, such as e.g. sucrose or glucose, and optionally an inorganic source of nitrogen, such as e.g. ammonium sulfate. Alternatively, these and other components can also be fed in separately.

During the growth or production phase, the temperature is established in a range from 29° C. to 42° C., preferably 33° C. to 40° C. Temperatures in a range from 27° C. to 39° C.

are also possible. The fermentation can be carried out under normal pressure or optionally under increased pressure, preferably under an increased pressure of 0 to 1.5 bar. The oxygen partial pressure is regulated at 5 to 50%, preferably approx. 20% atmospheric saturation. Regulation of the pH to a pH of approx. 6 to 8, preferably 6.5 to 7.5, can be effected with 25% aqueous ammonia.

The process according to the invention is distinguished with respect to conventional processes above all by an increased space/time yield or productivity.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A laboratory manual (1989) Cold Spring Harbor Laboratory Press). Unless described otherwise, the transformation of *Escherichia coli* was carried out by the method of Chung et al. (Proceedings of the National Academy of Sciences of the United States of America USA (1989) 86: 2172-2175).

EXAMPLE 1

Preparation of the *Escherichia coli* K-12 strain DM1265

A plasmid-free variant of the *E. coli* strain 472T23 was obtained from the American Type Culture Collection (Manasas, Va., USA) as ATCC98082. The strain ATCC98082 is described in the patent specification U.S. Pat. No. 5,631,157. The *E. coli* strain VL334/pYN7 was obtained from the Russian National Collection of Industrial Microorganisms (VKPM, Moscow, Russia) as CMIM B-1684. The strain CMIM B-1684 is described in the patent specification U.S. Pat. No. 4,278,765.

The plasmid pYN7 was isolated from the strain VL334/pYN7. A DNA fragment 6.25 kbp long which carries the thrABC operon was isolated from plasmid pYN7 by preparative agarose gel electrophoresis with the aid of the restriction enzymes HindIII and BamHI.

The plasmid pBR322 (Bolivar et al., Gene 2, 95-113 (1977)) was obtained from Pharmacia Biotech (Uppsala, Sweden) and treated with the restriction enzymes HindIII and BamHI. The DNA fragment 4.3 kbp long was isolated by preparative agarose gel electrophoresis. The two DNA fragments were mixed, treated with T4 DNA ligase, and the strain DH5α was transformed with the ligation mixture. After selection on ampicillin-containing (50 µg/mL) LB agar, transformants which contained a plasmid which corresponded in its structure to the plasmid pYN7 were obtained.

The plasmid was isolated from a transformant, cleaved partly with the enzyme EcoRI and completely with the enzyme HindIII and ligated with the parB gene region isolated. For this, the plasmid pKG1022 (Gerdes, Biotechnology (1988) 6:1402-1405) was cleaved with the enzymes EcoRI and HindIII, the cleavage batch was separated in 1% agarose gel and the parB fragment 629 bp in size was isolated with the aid of the QIAquick Gel Extraction Kit (QIAGEN, Hilden, Germany). The ligation mixture was employed for transformation of strain ATCC98082. Selection of plasmid-carrying cells was carried out on LB agar (Lennox, Virology 1:190 (1955)), to which 50 µg/ml ampicillin had been added. Successful cloning of the parB gene region could be detected after isolation of the plasmid DNA, control cleavage with EcoRI and HindIII and analysis of the cleavage batch by agarose gel electrophoresis. The plasmid was designated pYN7parB.

A transformant of the type ATCC98082/pYN7parB has been designated DM1265 and deposited in the form of a pure culture on Apr. 30 1999 at the Deutsche Sammlung fur Mikroorganismen und Zellkulturen (German Collection of Microorganisms and Cell Cultures=DSM, Braunschweig, Germany) as DSM12790 in accordance with the Budapest Treaty.

The strain DM1265 has, inter alia, an enhanced, "feed back" resistant aspartate kinase I-homoserine dehydrogenase I, an attenuated threonine deaminase, a resistance to at least 5 g/l L-threonine and the ability to utilize sucrose as a source of carbon.

This strain is distinguished by a high stability, in particular segregation stability.

Comparative Example A

Preparation of L-threonine with the aid of the *Escherichia coli* K-12 strain DM1265 by conventional fermentation An individual colony of the strain DM1265 was transinoculated on to minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l sucrose, 20 g/l agar, 50 mg/l ampicillin. The culture was incubated at 37° C. for approx. 5 days. 10 ml preculture medium with the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l sucrose, 50 mg/l ampicillin were inoculated with an inoculating loop and incubated for 16 (h) at 37° C. and 180 rpm on an ESR incubator from Kühner AG (Birsfelden, Switzerland).

A volume of 1 ml of this first preculture was inoculated into 1402 g of the nutrient medium A1-144. The culturing fermentation was carried out in 2 l stirred reactor fermenters from B. Braun (BBI, Germany, Melsungen, Biostat MD model). The nutrient medium A1-144 contained the constituents listed in Table 1. This second preculture was cultured for 22.5 h at a temperature of 37° C., a volume-specific gassing of 0.71 vvm (volume per volume per minute), an oxygen partial pressure of 10% of the atmospheric saturation and a pH of pH 7.0 until an optical density (OD) (660 nm) of 16.3 was reached.

For inoculation of 1233 g of the growth medium M1-463, which was contained in 2 l stirred reactor fermenters from B. Braun (BBI, Germany, Melsungen, Biostat MD model), 157.6 g of the second preculture in nutrient medium A1-144 were added. The growth medium M1-463 contained the constituents listed in Table 2. The culture was cultured at a temperature of 37° C., an aeration of 1l/min, a minimum stirring of 800 rpm and a pH of 7.0 and an oxygen partial pressure of 20% of the atmospheric saturation until a residual sugar concentration of approx. 3 g/l was reached. The broth obtained in this way was subsequently cultured for a further 30 h at a temperature of 37° C., an oxygen partial pressure of 20% of the atmospheric saturation and a pH of pH 7.0 until an OD (660 nm) of 33.4 was reached. During this time, 450 g of a production medium comprising a sucrose solution with a concentration of 650 g/l was fed in continuously.

The optical density (OD) was then determined with a digital photometer of the LP1W type from Dr. Bruno Lange GmbH (Berlin, Germany) at a measurement wavelength of 660 nm and the concentration of L-threonine formed was determined by ion exchange chromatography and post-column reaction with ninhydrin detection with an amino acid analyzer from Eppendorf-BioTronik (Hamburg, Germany), After 39.5 h, an L-threonine concentration of 69.6 g/l was found in the final fermentation sample. The space/time yield in this experiment was thus 1.76 g/l·h.

TABLE 1

Composition of nutrient medium A1-144

| Component | Concentration (per kg) |
|---|---|
| Sucrose | 30 g |
| Yeast extract | 2 g |
| $(NH_4)_2SO_4$ | 5 g |
| $K_2HPO_4$ | 2 g |
| NaCl | 0.6 g |
| $MgSO_4.7H_2O$ | 0.4 g |
| $FeSO_4.7H_2O$ | 20 mg |
| $MnSO_4.H_2O$ | 20 mg |
| Ampicillin | 50 mg |
| Structol | 0.3 g |

TABLE 2

Composition of growth medium M1-463

| Component | Concentration (per kg) |
|---|---|
| Sucrose | 27.7 g |
| Yeast extract | 1.87 g |
| NaCl | 0.62 g |
| $(NH_4)_2SO_4$ | 4.7 g |
| $K_2HPO_4$ | 1.9 g |
| $MgSO_4.7H_2O$ | 0.38 g |
| $MnSO_4.H_2O$ | 18 mg |
| $FeSO_4.7H_2O$ | 18 mg |
| Ampicillin | 50 mg |
| Structol | 0.1 g |

EXAMPLE 2

Preparation of L-threonine with the aid of the strain DM1265 with 2 subsequent feed processes and 10% inoculum in each case An individual colony of the strain DM1265 was transinoculated on to minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar, 50 mg/l ampicillin. The culture was incubated at 37° C. for approx. 5 days. 10 ml preculture medium with the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, 50 mg/l ampicillin were inoculated with an inoculating loop and incubated for 16 h at 37° C. and 180 rpm on an ESR incubator from Kühner AG (Birsfelden, Switzerland).

A volume of 1 ml of this first preculture was inoculated into 1402 g of the nutrient medium A1-144. The culturing fermentation was carried out in 2 l stirred reactor fermenters from B. Braun (BBI, Germany, Melsungen, Biostat MD model). The nutrient medium A1-144 contained the constituents listed in Table 1. This second preculture was cultured for 22.5 h at a temperature of 37° C., a volume-specific gassing of 0.71 vvm, an oxygen partial pressure of 10% of the atmospheric saturation and a pH of pH 7.0 until an OD (660 nm) of 16.3 was reached.

For inoculation of 1233 g of the growth medium M1-463, which was contained in 2 l stirred reactor fermenters from B. Braun (BBI, Germany, Melsungen, Biostat MD model), 157.6 g of the second preculture in nutrient medium A1-144 were added. The growth medium M1-463 contained the constituents listed in Table 2. The culture was cultured as described in Comparative Example A at a temperature of 37° C., an aeration of 1 l/min, a minimum stirring of 800 rpm and a pH of 7.0 and an oxygen partial pressure of 20% of the atmospheric saturation until a residual sugar concentration of approx. 3 g/l was reached after 9.5 h. The fermentation broth obtained in this way was then cultured for a further 30 h at a temperature of 37° C., an oxygen partial pressure of 20% of the atmospheric saturation and a pH of pH 7.0 until an OD (660 nm) of 33.4 was reached. During this time, 450 g of a production medium comprising a sucrose solution with a concentration of 650 g/l was fed in continuously. After the feed solution had been consumed and the residual sugar in the fermentation broth of this first run had been consumed, 90% of the fermentation broth (1656 g) of the fermenter contents was removed by pumping off.

The remaining 10% of the volume (184 g) was topped up with 1200 g of the growth medium M1-474 and the fermentation was started again. The growth medium M1-474 contained the constituents listed in Table 3. The culture of this second run was cultured as described in Comparative Example A at a temperature of 37° C., an aeration of 1 l/min, a minimum stirring of 800 rpm and a pH of 7.0 and an oxygen partial pressure of 20% of the atmospheric saturation until a residual sugar concentration of approx. 3 g/l was reached after 5 h. The broth was then cultured for a further 31.25 h at a temperature of 37° C., an oxygen partial pressure of 20% of the atmospheric saturation and a pH of pH 7.0 until an OD (660 nm) of 35.7 was reached. During this time, 450 g of a production medium comprising a sucrose solution with a concentration of 650 g/l was fed in continuously. After the feed solution had been consumed and the residual sugar in the fermentation broth had been consumed, 90% of the fermentation broth (1656 g) was removed from the fermenter by pumping off.

The remaining 10% of the total amount (184 g) was topped up with 1200 g of the growth medium M1-474 and the fermentation was started again. The growth medium M1-474 contained the constituents listed in Table 3. The culture of this third run was cultured as described in Comparative Example A at a temperature of 37° C., an aeration of 1 l/min, a minimum stirring of 800 rpm and a pH of 7.0 and an oxygen partial pressure of 20% of the atmospheric saturation until a residual sugar concentration of approx. 3 g/l was reached after 5.25 h. The culture was then cultured for a further 30.5 h at a temperature of 37° C., an oxygen partial pressure of 20% of the atmospheric saturation and a pH of pH 7.0 until an OD (660 nm) of 32.5 was reached. During this time, 450 g of a production medium comprising a sucrose solution with a concentration of 650 g/l was fed in.

At the end of each fermentation the OD and the concentration of L-threonine formed were determined as in Comparative Example A. The results of the particular runs are shown in Table 4.

The term "space/time" yield here describes the volumetric productivity, i.e. the quotient of the concentration of L-threonine at the end of the fermentation and the fermentation time.

TABLE 3

Composition of growth medium M1-474

| Component | Concentration (per kg) |
|---|---|
| Sucrose | 27.7 g |
| Yeast extract | 1.68 g |

TABLE 3-continued

Composition of growth medium M1-474

| Component | Concentration (per kg) |
|---|---|
| NaCl | 0.62 g |
| $(NH_4)_2SO_4$ | 4.7 g |
| $K_2HPO_4$ | 1.9 g |
| $MgSO_4.7H_2O$ | 0.38 g |
| $MnSO_4.H_2O$ | 18 mg |
| $FeSO_4.7H_2O$ | 18 mg |
| Ampicillin | 50 mg |
| Structol | 0.1 g |

TABLE 4

Results from Example 2

| Run | Time [h] | L-Threonine [g/l] | OD (660 nm) | Space/time yield [g/l · h] |
|---|---|---|---|---|
| 1 | 39.5 | 68.4 | 33.4 | 1.73 |
| 2 | 36.25 | 69.8 | 35.7 | 1.93 |
| 3 | 35.75 | 69.2 | 32.5 | 1.94 |

EXAMPLE 3

Preparation of L-threonine with the aid of the strain DM1265 with 4 subsequent feed processes and 25% inoculation in each case An individual colony of the strain DM1265 was transinoculated on to minimal medium with the following composition: 3.5 g/l $Na_2HPO_4*2H_2O$, 1.5 g/l $KH_2PO_4$, 1 g/l $NH_4Cl$, 0.1 gil $MgSO_4*7H_2O$, 2 g/l glucose, 20 g/l agar, 50 mg/l ampicillin. The culture was incubated at 37° C. for approx. 5 days. 10 ml preculture medium with the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, 50 mg/l ampicillin were inoculated with an inoculating loop and incubated for 16 h at 37° C. and 180 rpm on an ESR incubator from Kühner AG (Birsfelden, Switzerland).

A volume of 1 ml of this first preculture was inoculated into 1402 g of the nutrient medium A1-144. The culturing fermentation was carried out in 2 l stirred reactor fermenters from B. Braun (BBI, Germany, Melsungen, Biostat MD model). The nutrient medium A1-144 contained the constituents listed in Table 1. This second preculture was cultured for 22.5 h at a temperature of 37° C., a volume-specific gassing of 0.71 vvm, an oxygen partial pressure of 10% of the atmospheric saturation and a pH of pH 7.0 until an OD (660 nm) of 16.3 was reached.

For inoculation of 1233 g of the growth medium M1-463, which was contained in 2 l stirred reactor fermenters from B. Braun (BBI, Germany, Melsungen, Biostat MD model), 157.6 g of the second preculture in nutrient medium A1-144 were added. The growth medium M1-463 contained the constituents listed in Table 2. The culture was cultured as described in Comparative Example A at a temperature of 37° C., an aeration of 1 l/min, a minimum stirring of 800 rpm and a pH of 7.0 and an oxygen partial pressure of 20% of the atmospheric saturation until a residual sugar concentration of approx. 3 g/l was reached after 9.5 h. The fermentation broth obtained in this way was then cultured for a further 32 h at a temperature of 37° C., an oxygen partial pressure of 20% of the atmospheric saturation and a pH of pH 7.0 until an OD (660 nm) of 35.8 was reached. During this time, 450 g of a production medium comprising a sucrose solution with a concentration of 650 g/l was fed in continuously. After the feed solution had been consumed and the residual sugar in the fermentation broth of this first run had been consumed, 75% of the fermentation broth of the fermenter contents was removed by pumping off. The first fermentation (first run) was ended after 41.5 h and reached a titre of 67.1 g/l threonine.

The remaining 25% of the total amount (453 g) was topped up with 700 g of the growth medium M1-527 and the fermentation was started again. The growth medium M1-527 contained the constituents listed in Table 5. The culture of this second run was cultured as described in Comparative Example A at a temperature of 37° C., an aeration of 1 l/min, a minimum stirring of 800 rpm and a pH of 7.0 and an oxygen partial pressure of 20% of the atmospheric saturation until a residual sugar concentration of approx. 3 g/l was reached. The culture was then cultured for a further 30 h at a temperature of 37° C., an oxygen partial pressure of 20% of the atmospheric saturation and a pH of pH 7.0 until an OD (660 nm) of 36.2 was reached. During this time, 450 g of a production medium comprising a sucrose solution with a concentration of 650 g/l was fed in as in the first run. The draining off of the fermentation broth to 25% and the topping up of the fermenter with M1-527 was repeated a total of four times.

At the end of each fermentation the OD and the concentration of L-threonine formed were determined as in Comparative Example A.

Table 6 shows the results of the particular runs. The term "Total L-threonine formed" relates to the L-threonine effectively formed or produced during the fermentation run. To calculate the total L-threonine formed, the amount of L-threonine introduced by the inoculum is subtracted from the amount of L-threonine present in the fermentation tank at the end of the run. The term "Productivity" designates the quotient of the total L-threonine formed per fermentation run and the fermentation time per run.

TABLE 5

Composition of growth medium M1-527

| Component | Concentration (per kg) |
|---|---|
| Sucrose | 34.10 g |
| Yeast extract | 2.31 g |
| NaCl | 0.76 g |
| $(NH_4)_2SO_4$ | 5.78 g |
| $K_2HPO_4$ | 2.314 g |
| $MgSO_4.7H_2O$ | 0.464 g |
| $MnSO_4.H_2O$ | 22.7 mg |
| $FeSO_4.7H_2O$ | 22.7 mg |
| Ampicillin | 60 mg |
| Structol | 120 mg |

TABLE 6

Results from Example 3

| Run | Time [h] | L-Threonine [g/l] | OD (660 nm) | Total L-Threonine formed [g] | Productivity [g/h] |
|---|---|---|---|---|---|
| 1 | 41.5 | 67.1 | 35.8 | 120.7 | 2.91 |
| 2 | 35.7 | 74.5 | 36.2 | 100.5 | 2.82 |
| 3 | 34.5 | 80.0 | 31.4 | 108.0 | 3.13 |

TABLE 6-continued

Results from Example 3

| Run | Time [h] | L-Threonine [g/l] | OD (660 nm) | Total L-Threonine formed [g] | Productivity [g/h] |
|---|---|---|---|---|---|
| 4 | 35.0 | 76.3 | 33.4 | 103.0 | 2.94 |
| 5 | 41.5 | 73.0 | 31.7 | 98.6 | 2.37 |

Comparative Example B

Preperation of L-threonine with the aid of the i Escherichia coliK-12 strain kat-13 by conventional fermentation The L-threonine-producing *E. coli* strain kat-13 is described in U.S. Pat. No. 5,939,307 and deposited at the Agriculture Research Service Patent Culture Collection (Peoria, Ill., USA) as NRRL B-21593.

The strain kat-13 has, inter alia, an enhanced, "feed back" resistant aspartate kinase I-homoserine dehydrogenase I, an attenuated threonine dehydrogenase, resistance to borrelidin and the ability to utilize sucrose as a source of carbon.

An individual colony of the strain kat-13 was transinoculated on to minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar. The culture was incubated at 37° C. for approx. 5 days. 10 ml preculture medium with the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, were inoculated with an inoculating loop and incubated for 16 h at 37° C. and 180 rpm on an ESR incubator from Kühner AG (Birsfelden, Switzerland).

A volume of 0.45 ml of this first preculture was inoculated into 1500 g of the nutrient medium A1-158. The culturing fermentation was carried out in 2 l stirred reactor fermenters from B. Braun (BBI, Germany, Melsungen, Biostat MD model). The nutrient medium A1-158 contained the constituents listed in Table 7. This second preculture was cultured for 19.75 h at a volume-specific gassing of 1.16 vvm, an oxygen partial pressure of 20% of the atmospheric saturation and a pH of pH 6.9 until all the glucose had been consumed. The fermentation was started at Ha temperature of 39° C., and after a fermentation time of 18 h the temperature was lowered to 37° C.

For inoculation of 725 g of the growth medium M1-530, which was contained in 2 l stirred reactor fermenters from B. Braun (BBI, Germany, Melsungen, Biostat MD model), 110 g of the second preculture in nutrient medium A1-158 were added. The growth medium M1-530 contained the constituents listed in Table 8. The culture was cultured at a temperature of 37° C., an aeration of 1.3 l/min, a minimum stirring of 800 rpm and a pH of 7.0 and an oxygen partial pressure of 20% of the atmospheric saturation until all the glucose initially introduced had been consumed after 8 h. The fermentation broth obtained in this way was then cultured for a further 57 h at a temperature of 37° C., an oxygen partial pressure of 20% of the atmospheric saturation, an aeration of 1.5 l/min and a pH of pH 7.0. During this time, 1000 g of a production medium comprising a glucose·$H_2O$ solution with a concentration of 550 g/l was fed in continuously.

The OD and the concentration of L-threonine formed were then determined as in Comparative Example A.

After 65 h, an L-threonine concentration of 101.3 g/l was found in the final fermentation sample. The space/time yield in this experiment was thus 1.56 g/l·h.

TABLE 7

Composition of nutrient medium A1-158

| Component | Concentration (per kg) |
|---|---|
| Glucose.$H_2O$ | 88 g |
| Corn steep liquor (50%) | 20 g |
| $(NH_4)_2SO_4$ | 0.5 g |
| $KH_2PO_4$ | 2.5 g |
| Citric acid | 0.192 g |
| $MgSO_4.7H_2O$ | 2 g |
| $FeSO_4.7H_2O$ | 30 mg |
| $MnSO_4.H_2O$ | 21 mg |
| Kanamycin | 50 mg |
| Structol | 0.3 g |

TABLE 8

Composition of growth medium M1-530

| Component | Concentration (per kg) |
|---|---|
| Glucose.$H_2O$ | 88 g |
| Corn steep liquor (50%) | 20 g |
| Citric acid | 0.192 g |
| $(NH_4)_2SO_4$ | 0.5 g |
| $KH_2PO_4$ | 2.5 g |
| $MgSO_4.7H_2O$ | 2.0 g |
| $MnSO_4.H_2O$ | 21 mg |
| $FeSO_4.7H_2O$ | 30 mg |
| Kanamycin | 50 mg |
| Structol | 0.3 g |

EXAMPLE 4

Preparation of L-threonine with the aid of the strain kat-13 with a subsequent feed process and 10% inoculation An individual colony of the strain kat-13 was transinoculated on to minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar. The culture was incubated at 37° C. for approx. 5 days. 10 ml preculture medium with the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, were inoculated with an inoculating loop and incubated for 16 h at 37° C. and 180 rpm on an ESR incubator from Kühner AG (Birsfelden, Switzerland).

A volume of 0.45 ml of this first preculture was inoculated into 1500 g of the nutrient medium A1-158. The culturing fermentation was carried out in 2 l stirred reactor fermenters from B. Braun (BBI, Germany, Melsungen, Biostat MD model). The nutrient medium A1-158 contained the constituents listed in Table 7. This second preculture was cultured for 19.75 h at a volume-specific gassing of 1.16 vvm, an oxygen partial pressure of 20% of the atmospheric saturation and a pH of pH 6.9 until all the glucose had been consumed. The fermentation was started at a temperature of 39° C., and after a fermentation time of 18 h the temperature was lowered to 37° C. For inoculation of 725 g of the growth medium M1-530, which was contained in 2 l stirred reactor fermenters from B. Braun (BBI, Germany, Melsungen, Biostat MD model), 110 g of the second preculture in nutrient medium A1-158 were added. The growth medium M1-530 contained the constituents listed in Table 8. The culture was cultured at a temperature of 37° C., an aeration of 1.3 1/min, a minimum stirring of 800 rpm and a pH of 7.0 and an oxygen partial pressure of 20% of the atmospheric saturation until all the glucose initially introduced had been consumed after 8 h. The fermentation broth obtained in this way was then cultured for a further 57 h at a temperature of 37° C., an oxygen partial pressure of 20% of the atmospheric saturation, an aeration of 1.5 1/min and a pH of pH 7.0 until an OD (660 nm) of 46.4 was reached. During this time, 1000 g of a production medium comprising a glucose·$H_2O$ solution with a concentration of 550 g/l was fed in continuously. After the feed solution had been consumed and the residual sugar in the fermentation broth of this first run had been consumed, 90% of the fermentation broth (1651 g) of the fermenter contents was removed by pumping off.

The remaining 10% of the volume (184 g) was topped up with 650 g of the growth medium M1-531 and the fermentation was started again. The growth medium M1-531 contained the constituents listed in Table 9. The culture was cultured at a temperature of 37° C., an aeration of 1.5 1/min, a minimum stirring of 800 rpm and a pH of 7.0 and an oxygen partial pressure of 20% of the atmospheric saturation. During this time, 1000 g of a production medium comprising a glucose·$H_2O$ solution with a concentration of 550 g/l was fed in continuously.

At the end of each fermentation the OD and the concentration of L-threonine formed were determined as in Comparative Example A.

The results of the two runs are shown in Table 10. The term "Total L-threonine formed" relates to the L-threonine effectively formed or produced during the fermentation run. To calculate the total L-threonine formed, the amount of L-threonine introduced by the inoculum is subtracted from the amount of L-threonine present in the fermentation tank at the end of the run. The term "Productivity" designates the quotient of the total L-threonine formed per fermentation run and the fermentation time per run.

TABLE 9

Composition of growth medium M1-531

| Component | Concentration (per kg) |
| --- | --- |
| Corn steep liquor (50%) | 22.3 g |
| Citric acid | 0.214 g |
| $(NH_4)_2SO_4$ | 0.56 g |
| $KH_2PO_4$ | 2.79 g |
| $MgSO_4 \cdot 7H_2O$ | 2.23 g |
| $MnSO_4 \cdot H_2O$ | 24 mg |
| $FeSO_4 \cdot 7H_2O$ | 34 mg |
| Kanamycin | 50 mg |
| Structol | 0.3 g |

TABLE 10

Results of Example 4

| Run | Time [h] | L-Threonine [g/l] | OD (660 nm) | total L-Threonine formed [g] | Productivity [g/h] |
| --- | --- | --- | --- | --- | --- |
| 1 | 65.0 | 101.3 | 46.4 | 159.5 | 2.45 |
| 2 | 59.0 | 102.6 | 49.0 | 147.9 | 2.51 |

Comparative Example C

Preparation of L-threonine with the aid of the *Escherichia coli* K-12 strain B-3996 by conventional fermentation The L-threonine-producing *E. coli* strain B-3996 is described in U.S. Pat. No. 5,175,107 and deposited at the Russian National Collection for Industrial Microorganisms (VKPM, Moscow, Russia).

The strain B-3996 has, inter alia, an enhanced, "feed back" resistant aspartate kinase I-homoserine dehydrogenase I, an attenuated threonine deaminase, an attenuated threonine dehydrogenase, a resistance to at least 5 g/l L-threonine and the ability to utilize sucrose as a source of carbon.

An individual colony of the strain B-3996 was transinoculated on to minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l sucrose, 20 g/l agar, 20 µg/ml streptomycin. The culture was incubated at 37° C. for approx. 5 days. 10 ml preculture medium with the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l sucrose, 20 µg/ml streptomycin were inoculated with an inoculating loop and incubated for 16 h at 37° C. and 180 rpm on an ESR incubator from Kühner AG (Birsfelden, Switzerland).

A volume of 20 ml of this first preculture was inoculated into 1000 g of the nutrient medium A1-160. The culturing fermentation was carried out in 2 l stirred reactor fermenters from B. Braun (BBI, Germany, Melsungen, Biostat MD model). The nutrient medium A1-160 contained the constituents listed in Table 11. This second preculture was cultured for 14 h at a temperature of 37° C., a volume-specific gassing of 1.00 vvm, an oxygen partial pressure of 10% of the atmospheric saturation and a pH of pH 6.9 until all the sucrose had been consumed.

For inoculation of 1000 g of the growth medium M1-546, which was contained in 2 l stirred reactor fermenters from B. Braun (BBI, Germany, Melsungen, Biostat MD model), 100 g of the second preculture in nutrient medium A1-160 were added. The growth medium M1-546 contained the constituents listed in Table 12. The culture was cultured at a temperature of 37° C., an aeration of 1.0 1/min, a minimum stirring of 800 rpm and a pH of 6.9 and an oxygen partial pressure of 20% of the atmospheric saturation until all the sucrose initially introduced had been consumed after 7 h. The fermentation broth obtained in this way was then cultured for a further 29 h at a temperature of 37° C., an oxygen partial pressure of 20% of the atmospheric saturation, an aeration of 1.0 1/min and a pH of pH 6.9. During this time, a production medium comprising a sucrose solution with a concentration of 600 g/kg was fed in such that the sucrose concentration was always above 0.5 g/l.

The optical density (OD) was then determined with a digital photometer of the LP1W type from Dr. Bruno Lange GmbH (Berlin, Germany) at a measurement wavelength of 660 nm and the concentration of L-threonine formed was determined by ion exchange chromatography and post-column reaction with ninhydrin detection with an amino acid analyzer from Eppendorf-BioTronik (Hamburg, Germany), 63.8 g L-threonine were produced in the fermentation in 36 h. The productivity in this experiment was thus 1.77 g/h.

TABLE 11

Composition of nutrient medium M1-160

| Component | Concentration (per kg) |
| --- | --- |
| Sucrose | 40 g |
| Yeast extract | 2 g |
| $(NH_4)_2SO_4$ | 5 g |
| $KH_2PO_4$ | 2 g |
| $MgSO_4 \cdot 7H_2O$ | 0.4 g |
| $FeSO_4 \cdot 7H_2O$ | 20 mg |
| $MnSO_4 \cdot H_2O$ | 20 mg |
| Streptomycin | 100 mg |
| Structol | 0.2 g |

TABLE 12

Composition of growth medium M1-546

| Component | Concentration (per kg) |
| --- | --- |
| Sucrose | 30 g |
| Yeast extract | 2 g |
| $(NH_4)_2SO_4$ | 5 g |
| $KH_2PO_4$ | 2 g |
| $MgSO_4 \cdot 7H_2O$ | 0.4 g |
| $MnSO_4 \cdot H_2O$ | 20 mg |
| $FeSO_4 \cdot 7H_2O$ | 20 mg |
| NaCl | 0.6 |
| Structol | 0.3 g |

EXAMPLE 5

Preparation according to the invention of L-threonine with the aid of the *Escherichia coli* K-12 strain B-3996 with 5 subsequent feed processes and 10% inoculation in each case For inoculation of 1000 g of the growth medium M1-546, which was contained in 2 l stirred reactor fermenters from B. Braun (BBI, Germany, Melsungen, Biostat MD model), 100 g of the second preculture in nutrient medium A1-160 were added, as described in Example 7. The growth medium M1-546 contained the constituents listed in Table 12. The culture was cultured at a temperature of 37° C., an aeration of 1.0 l/min, a minimum stirring of 800 rpm and a pH of 6.9 and an oxygen partial pressure of 20% of the atmospheric saturation until all the sucrose initially introduced had been consumed after 7 h. The fermentation broth obtained in this way was then cultured for a further 29 h at a temperature of 37° C., an oxygen partial pressure of 20% of the atmospheric saturation, an aeration of 1.0 l/min and a pH of pH 6.9. During this time, 411.8 g of a production medium comprising a sucrose solution with a concentration of 600 g/kg was fed in continuously.

The fermentation broth was then drained off to 10% of the total amount. The remaining 10% of the total amount was topped up with growth medium M1-546 to the starting weight of 1100 g and the fermentation was started again. The growth medium M1-546 contained the constituents listed in Table 13. The culture of this third run was cultured as described in Example 7 at a temperature of 37° C., an aeration of 1 l/min, a minimum stirring of 800 rpm and a pH of 6.9 and an oxygen partial pressure of 20% of the. atmospheric saturation until all the sucrose initially introduced had been consumed after 8 h. The culture was then cultured for a further 28 h at a temperature of 37° C., an oxygen partial pressure of 20% of the atmospheric saturation and a pH of pH 6.9. During this time, a production medium comprising a sucrose solution with a concentration of 600 g/kg was fed in such that the sucrose concentration in the fermenter was always above 0.5 g/l. After a total of 36 h, the fermentation run was ended. The draining off of the fermentation broth to 10% and the topping up of the fermenter with M1-546 was repeated a total of five times.

At the end of each fermentation the OD and the concentration of L-threonine formed were determined as in Comparative Example A.

Table 13 shows the results of the particular runs. The term "Total L-threonine formed" relates to the L-threonine effectively formed or produced during the fermentation run. To calculate the total L-threonine formed, the amount of L-threonine introduced by the inoculum is subtracted from the amount of L-threonine present in the fermentation tank at the end of the run. The term "Productivity" designates the quotient of the total L-threonine formed per fermentation run and the fermentation time per run.

TABLE 13

Results of Example 5

| Run | Time [h] | L-Threonine yield [g/g sucrose] | OD (660 nm) | Total L-Threonine formed [g] | Productivity [g/h] |
| --- | --- | --- | --- | --- | --- |
| 1 | 36 | 22.7 | 39.1 | 63.8 | 1.77 |
| 2 | 36 | 25.9 | 26.2 | 45.2 | 1.26 |
| 3 | 36 | 19.9 | 39.0 | 47.5 | 1.32 |
| 4 | 36 | 27.5 | 40.0 | 79.3 | 2.20 |
| 5 | 36 | 21.3 | 40.0 | 63.2 | 1.76 |
| 6 | 36 | 26.3 | 41.7 | 82.4 | 2.29 | what is claimed is:

1. A process for the fermentative preparation of L-threonine, comprising:
    a) culturing an L-threonine-producing microorganism of the Enterobacteriaceae family;
    b) separating a portion of the fermentation broth produced in step a) such that 1 to 90 vol. % of the total volume of said fermentation broth remains in the fermentation tank;
    c) topping the fermentation broth remaining in said fermentation tank after step b) with growth medium and then continuing to culture said microorganism;
    d) repeating steps b) and c) one or more times; and
    e) isolating L-threonine from the fermentation broths collected.

2. The process of claim 1, wherein the culturing of said microorganism in step a) is by a fed batch process.

3. The process of either claim 1 or 2, wherein 1 to 50 vol. % of the total volume of said fermentation broth remains in said fermentation tank in step b).

4. The process of either claim 1 or 2, wherein 1 to 25 vol. % of the total volume of said fermentation broth remains in said fermentation tank in step b).

5. The process of either claim 1 or 2, wherein steps b) and c) are carried out two to six times.

6. The process of either claim 1 or 2, wherein said microorganism of the Enterobacteriaceae family is *Escherichia coli*.

7. The process of either claim 1 or 2, wherein, in step c), the fermentation broth remaining in the fermentation tank is topped with growth medium and, after 0 to 10 hours, production medium is added and further culturing of said microorganism is then carried out.

8. An L-threonine-producing and secreting microorganism of the Enterobacteriaceae family, wherein:
   a) aspartate kinase I-homoserine dehydrogenase I activity is enhanced in said microorganism;
   b) threonine deaminase activity is attenuated in said microorganism;
   c) said microorganism is resistant to feedback inhibition by at least 5 g/l of threonine;
   d) said microorganism has the ability to use sucrose as a source of carbon; and
   e) said microorganism comprises the parB gene region, wherein said parB gene region is a DNA fragment 629 bp in length and is isolated from the plasmid pYN7parB by cleaving said plasmid with EcoR1 and HindIII and then isolating said 629 bp fragment by electrophoresis.

9. The microorganism of claim 8, wherein said L-threonine-producing and secreting microorganism is deposited as deposit number DSM 12790 at German Collection of Microorganisms and Cell Cultures, Braunschweig, Germany.

10. A process for the fermentative preparation of L-threonine comprising:
   a) culturing the microorganism of either claim 8 or claim 9;
   b) separating a portion of the fermentation broth produced in step a) such that 1 to 90 vol. % of the total volume of said fermentation broth remains in the fermentation tank;
   c) topping the fermentation broth remaining in said fermentation tank after step b) with growth medium and continuing to culture said microorganism;
   d) repeating steps b) and c) one or more times; and
   e) isolating L-threonine from the fermentation broths collected.

11. The process of either claim 1 or 2, wherein said L-threonine-producing microorganism cultured in step a) of said process:
   a) has enhanced aspartate kinase I-homoserine dehydrogenase I activity;
   b) has attenuated threonine deaminase activity;
   c) is resistant to feedback inhibition by at least 5 g/l of threonine; and
   d) has the ability to use sucrose as a source of carbon.

12. The process of claim 11, wherein said L-threonine-producing microorganism has one or more characteristics selected from the group consisting of:
   a) resistance to feedback inhibition by borrelidin;
   b) resistance to inhibition by alpha-methylserine;
   c) resistance to inhibition by diaminosuccinic acid;
   d) sensitivity to fluoropyruvate;
   e) resistance to L-glutamic acid; and
   f) a need for L-methionine.

13. The process of claim 11, wherein said L-threonine-producing microorganism has attenuated threomne dehydrogenase activity.

14. The process of claim 11, wherein said L-threonine-producing microorganism is resistant to borrelidin.

15. The process of claim 11, wherein said L-threonine-producing microorganism has one or more characteristics selected from the group consisting of:
   a) resistance to feedback inhibition by at least 7% L-threonine; and
   b) a need for L-isoleucine.

16. The process of either claim 1 or 2, wherein said L-threonine-producing microorganism is deposited as deposit number DSM 12790 at the German Collection of Microorganisms and Cell Cultures, Braunschweig, Germany.

17. The process of either claim 1 or 2, wherein said L-threonine-producing microorganism is *E. Coli* strain NRRL B-21593 (kat-13).

18. The process of either claim 1 or 2 wherein said L-threonine-producing microorganism cultured in step a) of said process:
   a) has enhanced aspartate kinase I-homoserine dehydrogenase I activity;
   b) has attenuated threonine deaminase activity;
   c) is resistant to feedback inhibition by at least 5 g/l of threonine;
   d) has the ability to use sucrose as a source of carbon; and
   e) comprises parB gene region, wherein said parB gene region is a DNA fragment 629 bp in length and is isolated from the plasmid pyn7parB by cleaving said plasmid with EcoR1 and HindIII and then isolating said 629 bp fragment by electrophoresis.

* * * * *